United States Patent
Pell, Jr.

(10) Patent No.: US 6,211,398 B1
(45) Date of Patent: Apr. 3, 2001

(54) PROCESS FOR THE PREPARATION OF DIALKYL ESTERS OF NAPHTHALENEDICARBOXYLIC ACIDS

(75) Inventor: Thomas Michael Pell, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/150,107

(22) Filed: Sep. 9, 1998

Related U.S. Application Data

(60) Provisional application No. 60/060,888, filed on Oct. 3, 1997.

(51) Int. Cl.[7] .............................. C07C 67/54; B01D 3/06
(52) U.S. Cl. .............................. 560/78; 560/80; 560/98; 560/99; 560/100; 203/71; 203/73; 203/80; 203/88; 203/99; 203/DIG. 9; 203/DIG. 19
(58) Field of Search .......................... 560/80, 99, 100, 560/78, 98; 203/71, 81, 73, 80, 88, 99, DIG. 9, DIG. 19

(56) References Cited

U.S. PATENT DOCUMENTS

| | | |
|---|---|---|
| 3,227,743 | 1/1966 | Shaw et al. . |
| 4,003,948 | 1/1977 | Yamashita et al. . |
| 4,048,021 * | 9/1977 | Takamoto et al. ................. 203/91 |
| 5,095,135 | 3/1992 | Yamada et al. . |
| 5,254,719 * | 10/1993 | Holzhauer et al. ................. 560/78 |
| 5,262,560 * | 11/1993 | Holzhauer et al. ................. 560/78 |
| 5,350,874 | 9/1994 | Behrens et al. . |
| 6,013,831 * | 1/2000 | Machida et al. ................. 560/78 |

FOREIGN PATENT DOCUMENTS 7-233123   9/1995   (JP) .

* cited by examiner

*Primary Examiner*—Rosalynd Keys
(74) *Attorney, Agent, or Firm*—Rose M. Allen; Harry J. Gwinnell

(57) ABSTRACT

Disclosed is a process for the production and purification of dialkyl naphthalenedicarboxylate compounds wherein a crude naphthalenediacarboxylic acid is esterified with an alkanol such as methanol to produce a crude esterification product comprising dialkyl naphthalenedicarboxylate, starting materials and other compounds and the crude esterification product is purified by flash distillation to remove impurities which can cause fouling of conventional distillation equipment. A particularly useful diester is dimethyl 2,6-naphthalenedicarboxylate.

6 Claims, 3 Drawing Sheets

US 6,211,398 B1

PROCESS FOR THE PREPARATION OF DIALKYL ESTERS OF NAPHTHALENEDICARBOXYLIC ACIDS

CROSS REFERENCES TO RELATED APPLICATION

This application claims the benefit of U.S. Provisional Application Serial No. 60/060,888 filed Oct. 03, 1997.

FIELD OF THE INVENTION

This invention pertains to a process for the preparation of diesters of naphthalenedicarboxylic acids which are useful for preparing a variety of polyesters and polyamides. More specifically, this invention pertains to a process for the preparation of dialkyl naphthalenedicarboxylates wherein a crude naphthalenediacarboxylic acid is esterified with an alkanol such as methanol to produce a crude esterification product comprising dialkyl naphthalenedicarboxylate, starting materials and other compounds and the crude esterification product is purified by flash distillation to remove impurities which can cause fouling of conventional distillation equipment. A particularly useful diester is dimethyl 2,6-naphthalenedicarboxylate (2,6-NDC) which can be transesterified with ethylene glycol and the resulting ester can be polycondensed to make poly(ethylene-2,6-naphthalenedicarboxylate) (PEN) which can be formed into fibers, films and packaging materials with superior strength and barrier properties. To be acceptable as a starting material for PEN, 2,6-NDC should be substantially free of color bodies and other impurities.

BACKGROUND OF THE INVENTION 2,6-NDC is conveniently formed by the esterification of crude 2,6-naphthalenedicarboxylic acid (2,6-NDA) with methanol. Crude 2,6-NDA typically is contaminated with a variety of by-products such as trimellitic acid (TMA), brominated naphthalene compounds, and 6-formyl-2-naphthalenecarboxylic acid (FNA). The heavy metals such as cobalt and manganese used to catalyze the oxidation of 2,6-dimethylnaphthalene to 2,6-NDA form insoluble complexes, particularly with the TMA, and typically are included in the crude 2,6-NDA in excess of 1,000 ppm. The insoluble heavy metal complexes form deposits and foul heat exchangers in the esterification process, leading to frequent process interruptions for cleaning and maintenance. It is advantageous to remove the heavy metal contaminants at an early stage in the process to avoid problems in operations.

U.S. Pat. Nos. 5,254,719 and 5,095,135 disclose the use of sulfuric acid as a catalyst to esterify 2,6-NDA to 2,6-NDC. Sulfuric acid is effective at a relatively low temperature, e.g., about 130° C., and it reacts with the heavy metal impurities to form soluble sulfate salts. Disadvantages of sulfuric acid-catalyzed esterifications include corrosion of the reactor and the yield loss of methanol to dimethyl ether. Disposal of waste sulfates is another problem with the use of sulfuric acid catalysts. In addition, the reaction usually is carried out well under the melting point of 2,6-NDC (about 200° C.) to minimize or avoid the above mentioned problems with corrosion and dimethyl ether formation. Thus, the reaction is run in methanol solvent, resulting in a larger vessel for a given residence time relative to a reaction in which the excess methanol is substantially removed in the vapor phase.

U.S. Pat. Nos. 4,003,948 and 5,350,874 and Japanese Unexamined Patent Application (Kokai) 7-233123 disclose processes wherein the esterification is operated at higher temperatures with or without a metallic esterification catalyst. This method has the advantage of reduced dimethyl ether formation and corrosion. Disadvantages include generally higher pressure with no provision to reduce fouling by residual oxidation catalyst metals on heat exchanger or reactor surfaces. Without a provision to recycle incompletely esterified 2,6-NDA to the reactor, it is desirable to run the reaction at a high conversion. In a single backmixed reactor, high conversions are achieved at the expense of increased residence time and larger, more expensive reactors. Methods to narrow the residence time distribution, such as multiple reactors in series or devices to approach a tubular reactor like that disclosed in U.S. Pat. No. 5,350,874, are more expensive and add additional complexity to parts of the process subject to fouling. In the process disclosed in Japanese Unexamined Patent Application (Kokai) 7-233123, the 2,6-NDC is distilled following the reactor and methanol stripper, but the 2,6-NDC distillation is done under vacuum, and there is no provision to recycle partially converted 2,6-NDA. To avoid fouling in the distillation column base heater, it is necessary to dilute the residual oxidation catalyst metals with valuable 2,6-NDC, monomethyl ester of 2,6-naphthalenedicarboxylic acid (2,6-MHN), and 2,6-NDA, thus reducing the yield of 2,6-NDC. It is also necessary to operate the reactor at a high conversion to 2,6-NDC as there is no provision for concentration of the 2,6-NDC in the distillation.

U.S. Pat. No. 3,227,743 addresses some of these problems as they apply to the esterification of terephthalic acid (TPA) with methanol to produce dimethyl terephthalate (DMT) by operating a bubble column reactor under conditions such that the DMT product is removed as a vapor with excess methanol and the water of reaction. The lower vapor pressures of 2,6-DNC and the impurities present in crude 2,6-NDC have until now prevented a direct application to 2,6-NDC. There remains a need in the art for an efficient process for the manufacture of 2,6-NDC that minimizes fouling, operates at high rates, and presents a distilled product free of residual oxidation catalyst metals and other high boilers to a final purification process.

SUMMARY OF THE INVENTION

The present invention provides a novel process for the esterification of crude naphthalenedicarboxylic acids, preferably 2,6-NDA, to produce the corresponding esters, notably 2,6-NDC. Thus, my novel process provides a means for the manufacture of a dialkyl ester of a naphthalenedicarboxylic acid (NDC) which comprises the steps of:

(1) feeding an alkanol and a naphthalenedicarboxylic acid (NDA) to an esterification zone which is maintained at a temperature of about 200 to 350° C. to obtain a crude esterification product comprising alkanol, water, NDC, monoalkyl ester of naphthalenedicarboxylic acid (MHN), NDA, trialkyl trimellitate (TATM) and catalyst residues;

(2) removing liquid and vapor streams comprising crude esterification product from the esterification zone;

(3) reducing the pressure of the liquid and vapor streams of step (2) and feeding the streams to the lower section of a primary flash distillation column to produce (i) an overhead vapor stream rich in the NDC, alkanol and water and (ii) a column base underflow stream rich in NDA, MHN and NDC;

(4) recycling a major portion of the underflow stream of step (3) to the esterification zone;

(5) feeding a minor portion of the underflow stream of step (3) to a secondary flash vessel to produce a (i) vapor stream comprising NDC, MHN and NDA and (ii) liquid residue stream comprising TATM, catalyst residues, NDC, MHN and NDA; and (6) feeding the overhead vapor stream from step (3) and the vapor stream from step (5) to the mid-section of a second distillation column to obtain (i) an overhead vapor stream rich in alkanol and water and (ii) a column base underflow stream rich in NDC and essentially devoid of alkanol and water, wherein all of the heat for the primary flash distillation column and the secondary flash vessel is provided by the heat of the streams fed to the column and vessel and the alkanol contains up to about 4 carbon atoms. The process may be advantageously utilized to produce efficiently distilled NDC free or substantially free of residual oxidation catalyst and other high boilers at high yield and conversion. The NDC thus produced may then be further purified by crystallization, distillation, or other means known to those skilled in the art. Although the process may be used to produce any isomer of NDC from the corresponding NDA isomer, its value resides primarily in the manufacture of 2,6-NDA which, as noted above, is an important raw material for the production of poly(ethylene 2,6-naphthalenedicarboxylate).

BRIEF DESCRIPTION OF THE FIGURES

Accompanying

DETAILED DESCRIPTION OF THE INVENTION

Figure 1:
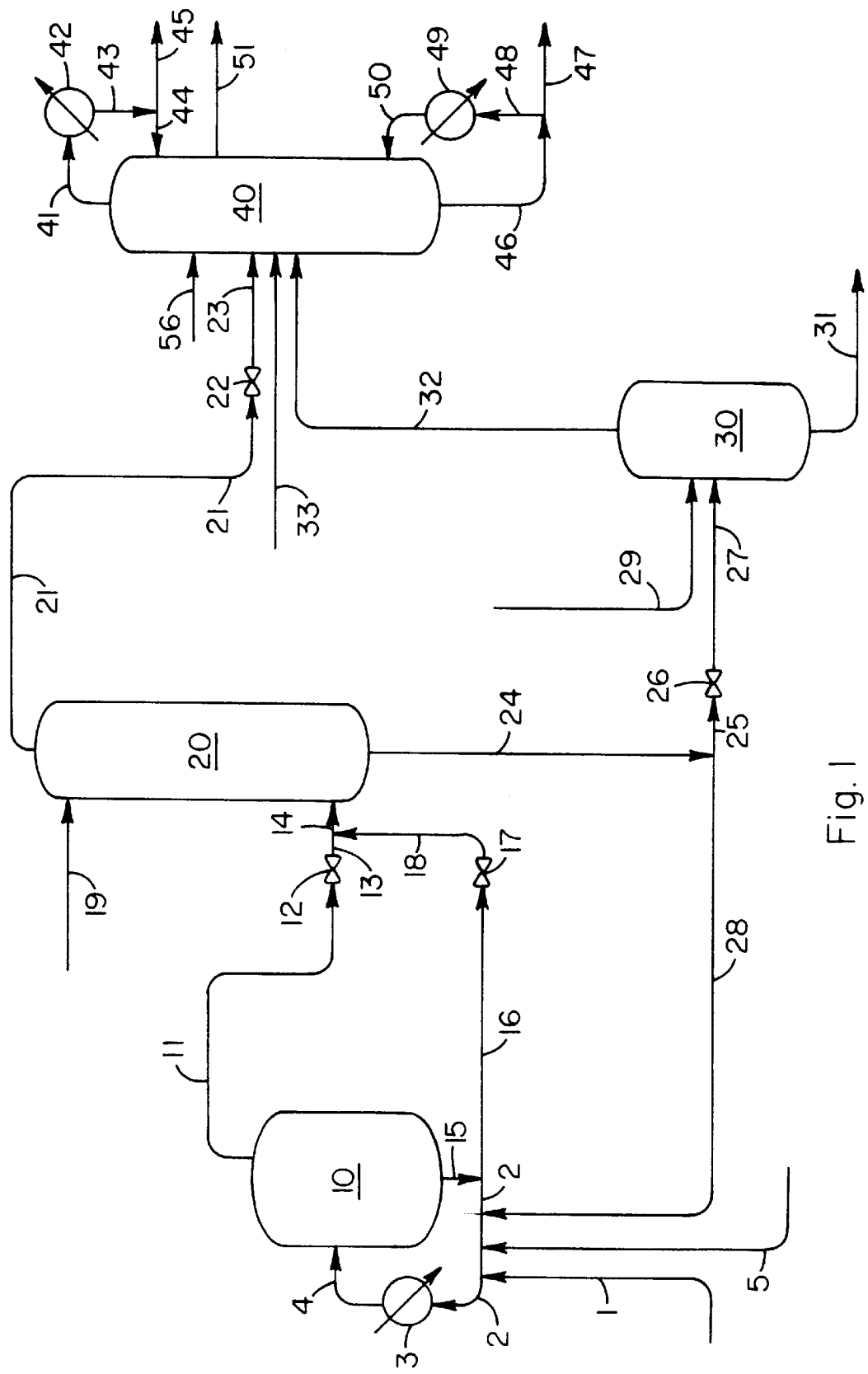
FIGS. 1, 2 and 3 are process flow diagrams illustrating an NDC production system embodying the principles of the process of the present invention. While the present invention is susceptible to embodiment in various forms, there is shown in FIGS. 1, 2 and 3 and hereinafter described in detail preferred embodiments of the invention. However, the present disclosure is to be considered as an exemplification of the invention without limitation to the specific embodiments illustrated.

In the first step of the process, a $C_1$–$C_4$ alkanol and a NDA are fed to an esterification zone comprising one or more reactors maintained at a temperature of about 200 to 350° C. to obtain a crude esterification product comprising lower alkanol, water, NDC, MHN, NDA, trialkyl trimellitate (TATM) and catalyst residues, e.g., cobalt and manganese metals, resulting from the catalyst system used to manufacture the NDA. The alkanol preferably is selected from ethanol and methanol and most preferably is methanol. The crude NDA employed in the process may be and normally is prepared by contacting a dialkylnaphthalene such as dimethylnaphthalene (DMN) or diisopropyinaphthalene with molecular oxygen in the presence of a catalyst system comprising cobalt, manganese and bromine and a reaction medium/solvent comprising a lower carboxylic acid, usually acetic acid. NDA so produced contains up to about 5 weight percent (based on the dry, total weight of the crude NDA) trimellitic acid (TMA), more typically about 0.1 to 1 weight percent TMA. Such crude NDA also contains up to 10,000 parts per million by weight (ppmw), e.g., 1000 to 10,000 ppmw, of oxidation catalyst residues comprising Co, Mn or a mixture thereof. Other impurities present in the crude NDA include formylnaphthalenecarboxylic acid, naphthalenecarboxylic acid, and various brominated compounds.

The crude NDA and methanol may be fed to the esterification zone as a slurry although other means known to the art may be used. For example, 2,6-NDA may be slurried in partially esterified material and the methanol fed as a vapor, thus partially reducing the load on the heater (reboiler) for the esterification zone. Although the esterification reaction requires two moles of methanol per mole 2,6-NDA, between 2.5 and 100, preferably between 6 to 50, moles of methanol per mole 2,6-NDA typically are fed to the esterification zone to drive the reaction and provide a means to entrain 2,6-NDC vapor into the primary flash distillation column without resorting to vacuum in the column or excessively high circulation rates between the first column and the reactor.

The reaction in the esterification zone is conducted at elevated temperature and pressure. For example, the temperature in the esterification zone normally is at least about 200° C. to avoid solids and plugging and below about 350° C. to avoid degradation of the reaction materials. Preferably, the temperature is between about 250 and 320° C. The pressure in the esterification zone is greater than or equal to about atmospheric (ambient) pressure and less than about 55 bar gauge (barg, about 800 pounds per square inch—psig), preferably between about atmospheric and about 17 barg (about 250 psig). Higher pressure will increase the reaction rate and reduce the residence time in the esterification zone but increasing pressure increases the circulation rate between the esterification zone and the primary flash distillation column. The reaction may be performed with any of the esterification catalysts known in the art to catalyze this reaction, such as, but not limited to Mo, Fe, or Ti, or it may be run without a catalyst. A significant advantage of the process of the present invention is that the esterification reaction does not need to be driven to complete or substantially complete conversion as the product ester will be concentrated in the primary flash distillation column. The higher carboxyl concentration in the esterification zone will result in a faster overall rate.

The reactor(s) of the esterification zone may be an agitated vessel, but a preferable design is a bubble column with a thermosiphon reboiler to avoid unnecessary seals and moving parts. The reactor is constructed of any suitable material which is not reactive with the process reactants under the conditions of the process of the present invention.

The pressures of the vapor and liquid streams withdrawn from the esterification zone are reduced by means of conventional valves, reducing the temperature and flashing a portion of the esterified and partially esterified naphthalenedicarboxylic acids. The vapor and liquid streams are fed to the lower section or base of the primary flash distillation column or to a vessel designed to intimately mix the vapor and liquid streams. The primary flash distillation column is not equipped with a reboiler or other heating means and, consequently, the circulation rate between the esterification zone and the primary flash distillation column must be sufficient to vaporize the product. A feature of this invention is that there is only one heat exchanger, a reboiler in the esterification zone, in contact with a potentially fouling material. A condenser may effect reflux on the primary flash distillation column, but a preferred method is to feed a solvent to the upper section or top of the primary flash distillation column. The solvent thus introduced will be vaporized and a portion of the esterified and partially esterified naphthalenedicarboxylic acids will be condensed. Thus, the desired dialkyl naphthalenedicarboxylate product will be partially purified. As the partially esterified compounds boil higher than the desired product, the bottom product, i.e., the column base underflow stream, from the primary flash distillation column will be enriched in the partially esterified compounds which may be recycled to the reaction zone. Another feature of the process of this invention is that separation of the desired diesters from partially esterified diacid and recycle of the partially esterified material to the esterification zone reduces the importance of driving the esterification reaction to completion. Thus, the esterification zone may be operated at conditions that favor incomplete conversion where the overall reaction rate is faster and the required residence time in the reactor is shorter.

A minor portion of the column base underflow stream from the primary flash distillation column is removed as a purge stream to dispose of residual oxidation catalysts, any esterification catalyst that has been added, and other high boilers. As the potential for fouling the reboiler of the esterification zone and other surfaces is related to the concentration of these catalyst residues and high boilers in the stream circulating between the esterification zone and the bottom of the primary flash distillation column, the high boiler concentration should be minimized. The concentration of high boilers in the circulating stream is proportional to the ratio of the flow rates of the purge stream to the fresh naphthalenedicarboxylic acid stream to the esterification zone. The weight ratio of the flow rates of the purge stream to the fresh naphthalenedicarboxylic acid feed to the esterification zone is between 0.005 and 0.50, preferably between 0.01 and 0.15.

To avoid loss of product, it is desirable to recover from the purge stream as much of the diester and partially converted diacid as is reasonably feasible. Accordingly, the pressure of the purge stream is reduced and the stream is fed to a secondary flash vessel along with a vaporized stream of the solvent advantageously utilized in the primary flash distillation column and the second distillation column. A portion of the purge stream is vaporized within the secondary flash vessel and the recovered valuable materials are fed as a vapor along with the vaporized solvent to a second distillation. Alternatively, if the concentration of incompletely esterified diacid in the vapor stream from the secondary flash vessel is high and further conversion of the incompletely esterified diacid is desirable, the stream may be condensed and recycled to the esterification zone.

Recovery of product by vaporization with solvent eliminates the need for the addition of heat, e.g., by means of a heat exchanger, to the secondary flash vessel. A variety of flash-type vessels are known in the art. The surfaces of the secondary flash vessel are subject to potential fouling but such a flash vessel is an inexpensive vessel and spares may be provided. The concentrated liquid purge stream leaving the secondary flash vessel may be discarded or it may be subjected to further processing by means known in the art to recover catalyst metals.

The overhead vapor stream from the primary flash distillation column and the vapor stream from the secondary flash vessel are fed to the mid-section of a second distillation column. Additional solvent also is fed to the second distillation column, preferably at the mid-section thereof. The pressure in the second distillation column is normally less than the pressure of the vapor streams from the primary flash distillation column and the secondary flash vessel to avoid expensive compression of the vapor from the aforementioned vessels. Pressures between about 20 torr and about 35 barg, preferably between about 100 torr about 3 barg, are acceptable. The distillation which occurs within the second column is carried out at temperatures in the range of about 50 to 375° C., for example, employing column base temperatures of about 150 to 375° C., depending upon the pressure within the column.

The water of reaction and excess alkanol are removed as an overhead vapor stream from the second distillation column. The column base underflow stream obtained from the second distillation column typically consists of at least 10, preferably 50 to 90 weight percent NDC, less than about 1 weight percent alkanol, less than 1 weight percent water and less than 10 weight percent TATM.

The solvent which is utilized in the process provided by the present invention may be selected from hydrocarbons, esters, aldehydes, acids, and ketones with boiling points higher than the alkanol and water in the overhead vapor stream from the second distillation column. A water-immiscible solvent is preferred to facilitate water removal. Preferred solvents include o-xylene, m-xylene, p-xylene 1-methylnaphthalene, methyl ethyl ketone, n-propyl acetate and heptane. The purpose of the solvent is to prevent solids from forming in the column by forming a liquid solution with the product. The total amount of solvent, i.e., the amount of additional solvent plus the solvent contained in the other stream fed to the second distillation column, fed to the second distillation column typically is about 5 to 90 weight percent, preferably 25 to 75 weight percent, of the total feed to the column. It is desirable to remove water in a concentrated stream by decanting an aqueous phase from a side draw stream from the second distillation column and returning the organic phase to second column.

The crude 2,6-NDC thus formed may be purified by crystallization or distillation. The prior art such as U.S. Pat. Nos. 5,254,719 and 5,095,135 and Japanese Published Unexamined Patent Application Heisei 7-233133, teaches purification by crystallization or a combination of crystallization and distillation. Crystallization and the requisite processes for separation of liquid from solids are difficult to operate, require numerous processing steps, are generally expensive, and require large energy use for distilling solvents. I have found that 2,6-NDC may be purified by distillation alone. In particular, it is possible to separate the close boiling 2,6-NDC and methyl 6-formyl-2-naphthalenecarboxylate (MFN) by distillation with a column having 10 to 100, preferably 26 to 60, stages in the stripping section. It is advantageous to remove a liquid stream from a stage with a high concentration of MFN and remove a concentrated MFN stream overhead, returning the bottoms to the original refining column. The solvent and lower boiling components such as trimethyl trimellitate (TMTM) and methyl naphthalenecarboxylate (MN) are removed overhead and the solvent is stripped and recycled. Alternatively, TMTM, MN and other lower boiling impurities may be recovered from side streams rich in these components to minimize energy use in solvent refining. The bottoms from the refining column, substantially free from solvent, MFN, and other low boilers, is distilled with the 2,6-NDC product removed overhead and the bottoms stream containing 2,6-MHN and 2,6-NDA recycled to the reactor to complete the esterification.

The above distillation/purification process which can be employed in conjunction with the ester manufacturing process of the present invention therefore comprises the steps of
(7) feeding the column base underflow stream from step (6) described hereinabove to the mid-section of a third distillation column to remove MFN and obtain a column base underflow stream rich in NDC, MHN and NDA; and
(8) feeding the column base underflow stream from step (7) to the mid-section of a fourth distillation column to obtain (i) an overhead vapor stream comprising substantially pure NDC and (ii) a column base undeflow stream rich in MHN and NDA.

Referring to accompanying FIG. 1, a mixture of NDA, MHN, NDC, methanol and any optional esterification catalysts are fed to reactor 10 comprising an esterification zone via lines 1, 2, heat exchanger 3 and line 4. Recycle material from primary flash distillation column 20 also is fed to reactor 10 via lines 24, 28, 2, heat exchanger 3 and line 4. The feed to esterification reactor 10 may also include a process recycle stream (line 5) which is obtained from the distillation process shown in FIG. 3 and described hereinafter in detail. The mixture fed to reactor 10 via line 4 typically comprises 0.1 to 30% NDA, 1 to 50% MHN, 1 to 50% NDC and 30 to 95% methanol with minor amounts of TMA and TAMA. (All percentages given herein are by weight unless specified otherwise.) Heat exchanger 3 maintains a temperature of about 20 to 375° C. within reactor 10 which is maintained at a pressure of about 0.5 to 70 barg. Residence time with reactor 10 typically is about 15 to 360 minutes. A product vapor stream is removed overhead from reactor 10 by means of line 11, passed through pressure reduction valve 12 and then fed via lines 13 and 14 to the base of primary flash distillation column 20. A liquid product underflow stream is removed from the base of reactor 10 by means of line 15, transferred to pressure reduction valve 17 via line 16 and then fed via lines 18 and 14 to the base of primary flash distillation column 20 along with the vapor product stream. The vapor stream from reactor 10 typically comprises 0.01 to 10% NDA, 1 to 30% MHN, 1 to 50% NDC, 0.01 to 5% TMTM and 40 to 90% methanol whereas the liquid stream from reactor 10 typically comprises 0.1 to 40% NDA, 1 to 40% MHN, 10 to 99% NDC, 0.01 to 5% methanol and 0.01 to 5% TMMA.

Primary flash distillation column 20 normally is operated at approximately atmospheric pressure or under mild vacuum, e.g., a pressure of about 0.05 to 2 bar absolute (bara). A primary feature of the present invention is the absence of a heat exchanger or other supplemental heat source for column 20. Thus, all of the heat required for the operation of column 20 is provided by the stream fed via line 14. The temperature at the base of column 20 may be in the range of about 200 to 375° C. and in the range of about 200 to 375° C. at the head of the column. In addition to the vapor and liquid effluents from reactor 10, a solvent such a xylene may be fed to the upper section of column 20 via line 19. The amount of solvent fed via line 19 per weight of material fed via line 14 typically gives a solvent:line 14 feed weight ratio of about 0.01:1 to 1:1. Column 20 typically is equipped with trays or packing material to increase the efficiency of the separation which occurs in the column.

An overhead vapor stream which contains from about 1 to 75% NDC is removed from column 20 by line 21, passed through optional pressure reduction valve 22 and fed via line 23 to the mid-section of second distillation column 40. A column base underflow is removed from primary flash distillation column 20 by means of line 24. The weight ratio of the overhead vapor stream (line 21) to the underflow liquid stream (line 24) may vary from about 25:1 to 1:1. The underflow stream typically comprises about 1 to 15% NDA, 1 to 75% MHN, 5 to 95% NDC, 0 to 5% methanol, 0 to 5% water, 0 to 10% TMMA, 0 to 5% TMA and the metal oxidation catalyst residues. The underflow stream removed from the base of column 20 by line 24 is split into two streams: (1) a recycle stream which is recycled to reactor 10 via lines 28 and 2, heat exchanged 3 and line 4; and (2) a purge stream which is fed by line 25, through pressure reduction valve 26 and line 27 to secondary flash vessel 30. The weight ratio of purge stream (2) to recycle stream (1) may be in the range of about 0.001:1 to 0.3:1.

The purpose of secondary flash vessel 30 is to recover a large portion, e.g., up to 95%, of the valuable components present in the stream fed to the vessel. The heat required to vaporize and recover these valuable components is provided by the heat contained in the line 27 stream plus heat provided by solvent which may be fed to vessel 30 via line 29. Typically, about 20 to 95% of the material fed via line 27 to vessel 30 is vaporized and transported by line 32 to the mid-section of second distillation column 40. A liquid purge stream is removed from the base of vessel 30 through line 31 and is discarded or, alternatively, subjected to further processing to recover valuable components, e.g., organics and oxidation catalyst components. This liquid purge stream typically comprises about 0.02 to 50% cobalt, bromine and other oxidation catalyst residues and is about 1 to 50% of the material fed to vessel 30.

The vapor stream from column 20 and vessel 30 are fed to the mid-section of second distillation column 40 for the purpose of separating unreacted alkanol and water of reaction from the NDC product. Additional solvent may be fed via line 33 to the mid-section of column 40. Column 40 typically is operated at a pressure of about 25 torr to 1.5 barg, a base temperature of about 100 to 250° C. and a column head temperature of about 25 to 200° C. Column 40 usually will be equipped with trays and/or packing material. An overhead vapor stream comprising alkanol, some of the solvent and water is removed from the upper section of column 40 by line 41. As depicted in the Figure, the overhead vapor stream may be condensed in heat exchanged 42 and a portion, e.g., up to 90% recycled as reflux via lines 43 and 44. The portion not recycled may be removed from the process via line 45 and discarded or subjected to further processing to recover alkanol.

Figure 2:
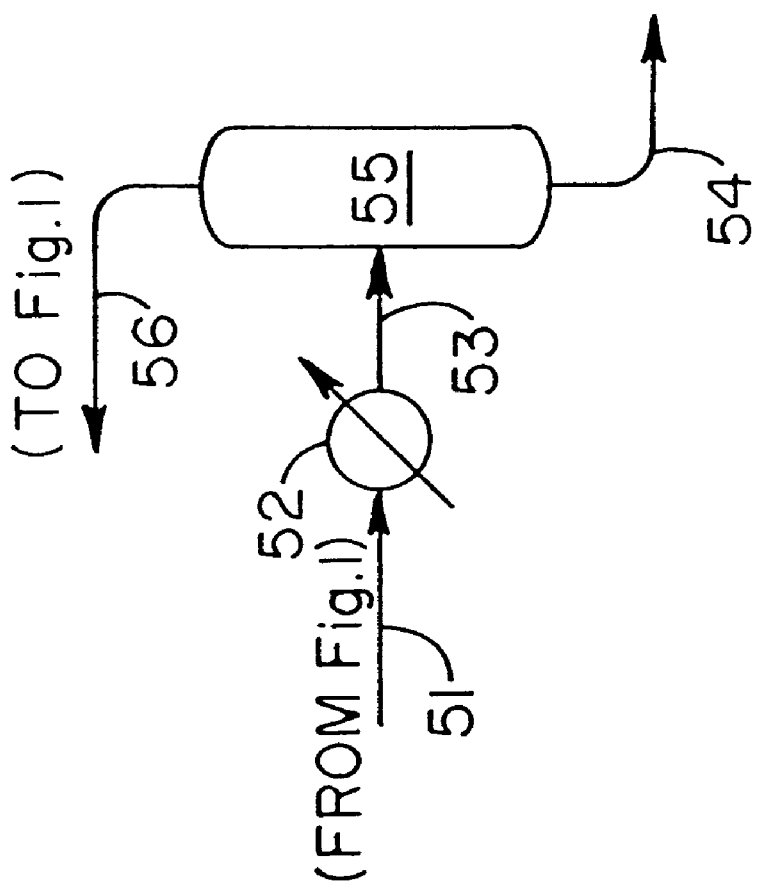

It is usually advantageous to remove the bulk of the water by removing a side stream from column 40 as shown in FIGS. 1 and 2. Thus, side stream 51 is removed from column 40 above the point or points at which lines 23, 32 and 33 enter column 40. Side stream 51 is cooled in heat exchanger 52 and fed via line 53 to decanter 55 wherein an alkanol- and solvent-rich organic phase separates from an aqueous phase. The organic phase is returned to column 40 via line 56. The aqueous phase is removed from decanter 55 through line 54 for disposal or recovery of residual alkanol and other valuable components. Side stream 51 contains between 5% and 95%, normally between 25% and 95%, water. Stream 53 normally is to 0 to 150° C., preferably to 40 to 80° C., to minimize the concentration of methanol and other organic components in the aqueous stream.

A liquid base product is removed from column 40 and the esterification/purification process of the present invention via lines 46 and 47. The liquid base product stream typically comprises at least 5%, preferably at least 30%, NDC. A portion of the liquid stream is returned to the lower section of column 40 by line 48, heat exchanger 49 and line 50 to provide the heat required for the operation of column 40. Since catalyst residues and most high boilers have been removed from the process via line 31, fouling and plugging of heat exchanger 49 does not occur or requires many hours of operation before it occurs.

Figure 3:
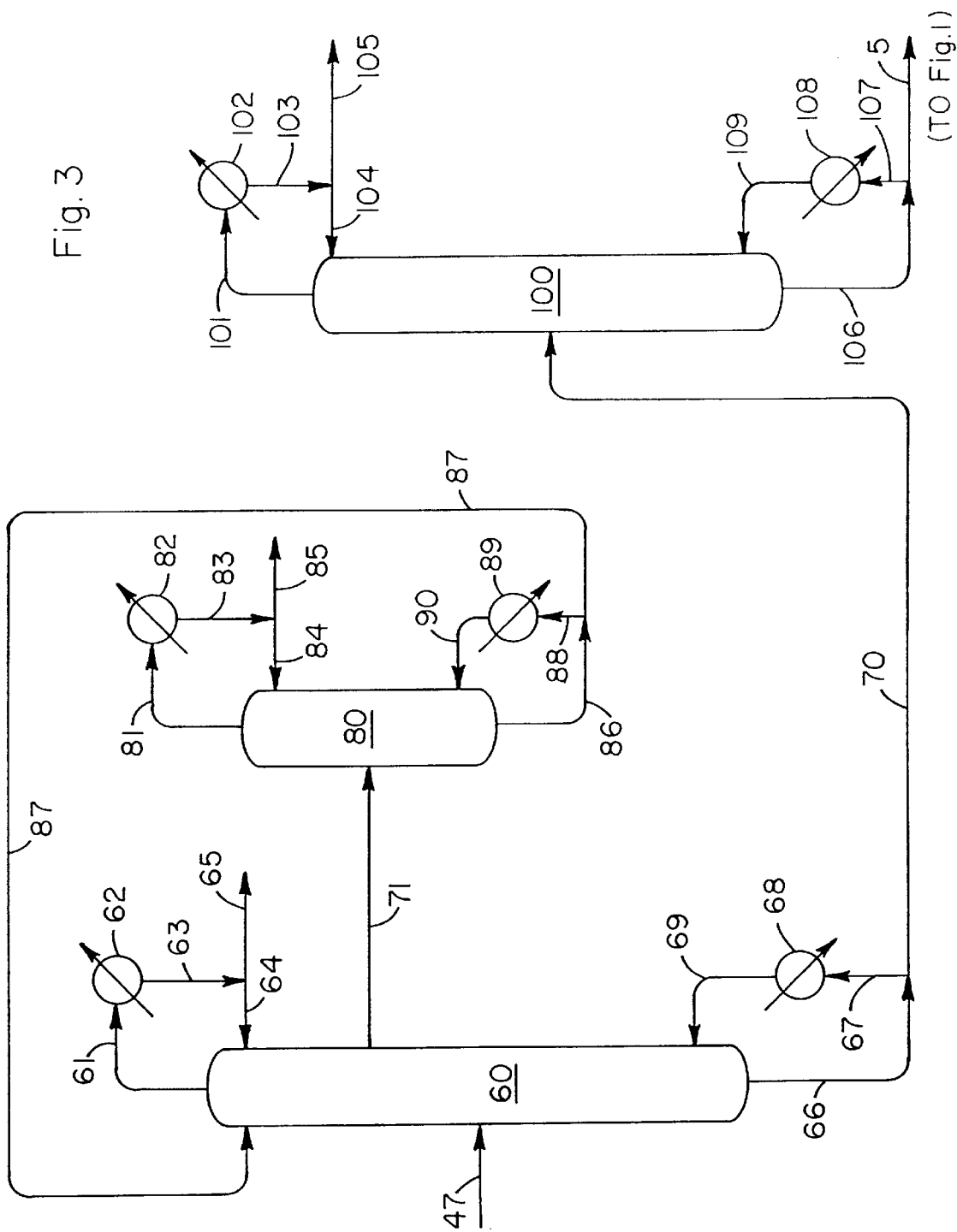

Accompanying FIG. 3 is a process flow diagram for a distillation process whereby the liquid base product obtained from column 40 via line 47 may be purified. The liquid base product is fed through line 47 to the mid-section of column 60 for the purpose of removing residual solvent and impurities that boil higher than the NDC product, notably MFN, TMTM, and MN. Column 60 typically is operated at a pressure of about 10 to 760 torr, preferably 20 to 200 torr, a base temperature of 200 to 374° C., and a column head temperature of 25 to 200° C. Column 40 normally is equipped with trays and/or packing material. As depicted in FIG. 3, an overhead vapor stream is removed from column 60 via line 61, condensed in heat exchanger 62 and a portion, e.g., up to 90%, of the condensed stream is recycled as reflux to column 60 via lines 63 and 64. The portion of stream 63 which is not recycled is removed from the process via line 65 and subjected to further processing to recover the solvent.

To avoid large energy costs encountered by a large solvent recycle stream in line 64, it is advantageous to remove a side stream, stream 71, from column 60 between the feed to column 60 and the top of column 60. Stream 71 is fed to column 80 wherein it is subjected to additional distillation for the purpose of separating the close-boiling MFN from NDC. Column 80 is typically operated at a pressure of 15 to 300 torr, a base temperature of 200 to 375° C., and a column head temperature of 200 to 360° C. Column 60 typically is equipped with trays and/or packing material. As shown in FIG. 3, an overhead vapor stream is removed from column 80 via line 81 and condensed in heat exchanger 82. A portion, e.g. up to 98%, of the material condensed in heat exchanger 82 is recycled as reflux to column 80 via lines 83 and 84. The portion not recycled is removed from the process via line 85 and discarded or subjected to further processing to recover valuable components.

A liquid base product is removed from column 80 via line 86 and returned to the upper section or top of column 60 by line 87. The liquid base product stream typically comprises at least 30%, and preferably 75%, NDC. A portion of the liquid base product stream is returned to the lower section of column 80 by line 88, heat exchanger 89, and line 90 to provide the heat required for the operation of column 80.

A liquid base product is removed from column 60 via line 66 and fed through line 70 to the mid-section of column 100. The liquid base product stream typically comprises at least 10%, preferably at least 40%, NDC. The remainder of stream 66 consists essentially of MHN and other volatile unesterified acids that boil lower than NDC. A portion of the liquid stream is returned to the lower section of column 60 via line 67, heat exchanger 68, and line 69 to provide the heat needed for the operation of column 60. Distillation column 100 separates essentially pure NDC product from MHN and other unesterified high boiling acids. Column 100 typically is operated at a pressure of about 10 to 500 torr, a base temperature of about 200 to 390° C., and a column head temperature of about 200 to 350° C. Column 100 normally is equipped with trays and/or packing material. An overhead vapor stream consisting of essentially pure NDC is removed from the upper section or top of column 100 by line 101. As depicted in FIG. 3, the overhead vapor stream may be condensed in heat exchanger 102 and a portion, e.g. up to 95%, recycled as reflux via lines 103 and 104. The portion of the overhead product stream which is not recycled is removed from the process by line 105. The product is essentially pure NDC, e.g., consisting of at least 99.9%, preferably 99.99%, NDC which is suitable for use in the manufacture of polyesters.

A liquid base underflow is removed from column 100 via lines 106. The liquid base underflow stream typically comprises between 1% and 95% MHN and is advantageously recycled to the esterification reactor, i.e., esterification reactor 10 of FIG. 1, via line 5 to complete the esterification to the desired NDC product. A portion of the liquid stream is returned to the lower section of column 100 by line 107, heat exchanger 108, and line 109 to provide the heat required for the operation of column 100.

EXAMPLES

The continuous operation of the esterification/purification process of the invention is further illustrated by the following examples. The examples are based on computer simulations of the process using esterification rates determined from the esterification procedure. The flow rates are given in parts by weight per hour and all percentages are by weight unless otherwise stated.

Esterification Procedure 300 g 2,6-NDC, 50 g crude 2,6-NDA, and 50 g 1-methyl naphthalene (1-MN) were mixed in a one-liter autoclave and heated to 305° C. Dry methanol was fed through a syringe pump at a rate of 37 mL per hour. The autoclave was fitted with a condenser with oil at 200° C. on the jacket, which served to reflux 1-MN, 2,6-NDC, and 2,6-MHN. The 1-MN was added to avoid solidification and plugging in the condenser and overhead lines. A control valve in the vent line controlled pressure. A small flow of nitrogen was introduced downstream of the condenser to facilitate action of the control valve. The esterification procedure was carried out in the absence of an esterification catalyst at 2.05 barg (30 psig) and at 6.8 barg (100 psig). The reaction mixtures were sampled after 2 hours and 4 hours and the samples were analyzed by gas chromatography. The results of these analyses are shown in Table I wherein Pressure is given in barg, Time is given in hours, the values given for 2,6-NDC, 2,6-MHN and 2,6-NDA are weight percentages based on the total weight of the reaction mixture and the Carboxyl values are moles total carboxyl per mole (2,6-NDA +2,6-MHN+2, 6-NDC). The samples analyzed were contaminated with residual MN.

TABLE I

| Pressure | Time | NDC | MHN | NDA | Carboxyl |
| --- | --- | --- | --- | --- | --- |
| 6.8 | 2 | 74.5 | 4.78 | 0.64 | 0.0739 |
| 6.8 | 4 | 73.7 | 0.81 | 0.49 | 0.0262 |
| 2.05 | 2 | 65.4 | 8.63 | 0.53 | 0.1378 |
| 2.05 | 4 | 84.0 | 4.68 | 0.39 | 0.0653 |

Example 1

A feed stream containing fresh 2,6-NDA and methanol and minor amounts of 2,6-MFN, TMA, 2-naphthoic acid (NA), and cobalt is fed to reactor 10 via lines 1 and 2, heat exchanger 3 and line 4 at a rate of 519 parts per hour in the process depicted in FIG. 1. A recycle stream comprising 2,6-NDC, methanol, water, 2,6-MHN, 2,6NDA, TMTM, MN 2,6-MFN and cobalt also is fed to reactor 10 via recycle line 28, line 2, heat exchanger 3 and line 4 at a rate of 1756 parts per hour. The reactor is modeled as a two-phase backmixed reactor. The esterification kinetics are first order in carboxyl with a coefficient of 0.649 hour$^{-1}$, derived from the 6.9 barg data from the esterification procedure. The temperature in reactor 10 is 305° C. and the pressure is 6.9 barg (100 psig). The liquid volume in reactor 10 is 1.27 cubic meters. As is evident to those skilled in the art, this residence time can be reduced by the use of an esterification catalyst such as Mo, Fe, or Ti at the expense of additional cost and insoluble components.

A vapor comprising methanol, water, 2,6-NDA, 2,6-MHN, 2,6-NDC, 2,6-MFN, 2,6-FNA, NA, MN, TMTM and TMA is removed continuously from reactor 10 by line 11, the pressure is reduced by valve 12 to 310 torr and the vapor stream is fed at a rate of 296 parts per hour via lines 13 and 14 to the base of primary flash distillation column 20 which is equipped with 10 plates. A liquid product underflow stream comprising methanol, water, 2,6-NDA, 2,6-MHN, 2,6-NDC, 2,6-MFN, 2,6-FNA, NA, MN, TMTM and TMA is removed continuously from reactor 10 by lines 15 and 16, passed through valve 17 wherein the pressure of the stream is reduced to 310 torr and the liquid stream is fed to the base of column 20 at a rate of 1979 parts per hour via lines 18 and 14. Reflux in column 20 is generated by introducing 74.3 parts per hour o-xylene via line 19 to the upper section of the column. The pressure within column 20 is approximately 300 torr, the column base temperature is about 271° C. and the column head temperature is approximately 253° C.

An overhead vapor stream is removed continuously from column 20 through line 21 at a rate of 617 parts per hour, passed through valve 22 wherein the pressure of the vapor stream is reduced to 284 torr and fed via line 23 to the mid-section of second distillation column 40 which contains 15 plates. A column underflow liquid is removed from column 20 by line 24 at a rate of 1732 parts per hour and 1708 parts of this stream are recycled to esterification reactor 10 via line 28. The 1,000-ppm Co in the crude 2,6-NDA feed is concentrated to 0.91 weight percent in the column 20 underflow. A purge stream is transferred by line 26 through valve 26 which reduces the pressure of the stream to about 297 torr, and then through line 27 to the mid-section of secondary flash vessel 30. o-Xylene having a temperature of 284° C. also is fed to the mid-section of vessel 30 via line 29 at a rate of 50.4 parts per hour. A vapor stream is removed from vessel 30 and transferred via line 32 to the mid-section of distillation column 40 at a rate of 69.9 parts per hour. A purge stream is removed from the process by line 31 at a rate of approximately 4.5 parts per hour.

In addition to the vapor streams fed via lines 23 and 32, o-xylene also is fed to the mid-section of second distillation column 40 at a rate of 151 parts per hour. The approximate conditions within column 40 are: pressure=258 torr, base temperature=127° C., head temperature=44° C. A vapor stream comprising methanol, water and o-xylene is removed continuously from colum 40 through line 41 at a rate of 598 parts per hour and fed to heat exchanger (condenser) 42 wherein the vapor is condensed. The condensed liquid and any uncondensed vapor is removed from heat exchanger 42 by line 43 and a portion is returned to the upper section of column 40 via line 44 at a rate of 266 parts per hour. The portion of the line 43 material not recycled to column 40 is removed from the process at a rate of 332 parts per hour.

A liquid base product is removed continuously from column 40 and the process by lines 46 and 47 at a rate of 506 parts per hour. A portion (147 parts per hour) of the liquid product of line 46 is transferred by line 48 to heat exchanger 49 wherein the liquid product is heated and then fed to the base of column 40 to provide for the heat for the operation of the column. The liquid bottoms product from column 40 contains 2,6-NDA, 2,6-MHN, 2,6-NDC, o-xylene, TMTM and methyl naphthalenecarboxylate. The liquid bottom stream is free of residual oxidation and esterification catalysts and concentrated in 2,6-NDC relative to 2,6-NDA and 2,6-MHN. It may be further purified by crystallization, preferably from oxylene, or by distillation. Purification by distillation, e.g., by the process depicted in FIG. 3 and described below, is preferred to avoid handling of solids and solvent recovery expenses inhereent in crystallization processes. The 2,6-NDA and 2,6-MHN present in the liquid product stream may be recycled to the esterification reactor after purification.

The composition (weight percentages) of certain of the streams of the process described above are set forth in Table II wherein MeOH is methanol and o-XYL is o-xylene. The values marked * are parts per million.

TABLE II

| Component | Stream | | | | | |
|---|---|---|---|---|---|---|
| | 1 | 5 | 13 | 18 | 24 | 31 |
| MeOH | 55.60 | — | 71.40 | — | — | — |
| Water | — | — | 12.20 | — | — | — |
| 2,6-NDC | — | 67.70 | 13.90 | 79.50 | 78.50 | 60.90 |
| 2,6-NDA | 41.60 | 1.71 | 0.29 | 5.52 | 6.35 | 15.50 |
| 2,6-MHN | — | 30.60 | 13.00 | 11.70 | 12.90 | 17.10 |
| TMTM | — | — | 0.70 | — | 0.79 | 0.19 |
| 2,6-FNA | 0.39 | — | — | — | — | — |
| TMA | 2.02 | — | — | — | — | — |
| o-XYL | — | — | — | — | — | 1.19 |
| NA | 0.33 | — | — | — | — | — |
| MN | — | — | 0.14 | 0.11 | 465* | — |
| 2,6-MFN | — | 5.4* | 0.10 | 0.49 | 0.46 | 0.29 |
| Cobalt | 444* | — | — | 0.84 | 0.95 | 5.86 |

| Component | Stream | | |
|---|---|---|---|
| | 32 | 41 | 46 |
| MeOH | — | 65.90 | — |
| Water | — | 11.70 | — |
| 2,6-NDC | 14.60 | — | 53.70 |
| 216-NDA | 0.74 | — | 0.15 |
| 2,6-MHN | 2.09 | — | 2.86 |
| TMTM | 0.17 | — | 2.50 |
| 2,6-FNA | — | — | — |
| TMA | — | — | — |
| o-XYL | 82.30 | 22.40 | 40.00 |
| NA | — | — | — |
| MN | — | 106* | 0.37 |
| 2,6-MFN | 2.91 | 881* | 0.42 |
| Cobalt | 4.86 | — | — |

Using the purification process depicted in FIG. 3, the liquid bottoms product from column 40 containing 2,6-NDA, 2,6-MHN, 2,6-NDC, o-xylene, 2,6-MFN, TMTM and methyl naphthalenecarboxylate (MN) is fed through line 47 to tray 10 of the 50 theoretical tray distillation column 60 at a rate 505.8 parts per hour. The approximate conditions within column 60 are: column head pressure=50 torr, column base pressure 150 torr, base temperature=306° C., head temperature=65° C. An overhead vapor stream comprising 2,6-NDC, MN, 2,6-MFN, TMTM, and o-xylene is removed via line 61 at a rate of 2270 parts per hour and condensed in heat exchanger 62. Two thousand sixty (2060) parts per hour of the condensed stream are recycled to the upper section of column 60 via lines 63 and 64 and the portion not recycled is removed from the process by lines 63 and 65. A side stream comprising 2,6-MFN, 2,6-NDC and TMTM is removed from tray 7 of column 60 at a rate of 60.9 parts per hour and fed to tray 15 of the 30 theoretical trays column 80 by means of line 71. The approximate conditions within column 80 are: head pressure=30 torr, base pressure=50 torr, base temperature=268° C., head temperature=202° C. An overhead vapor is removed from column 80 through line 81 at a rate of 190 parts per hour and condensed in heat exchanger 82. The ratio of the recycle flow via line 84 to take-off flow via line 85 is 12:1. The overhead product from column 80 contains 2,6-MFN, 2,6-NDC, and TMTM and represents the primary purge for 2,6-MFN, the most difficult component to separate from 2,6-NDC. The liquid bottom product from column 80 is recycled via line 87 to the top tray of column 60 at a rate of 46.3 parts per hour. Two hundred seven (207) parts per hour of the liquid bottom product is transferred from line 86 to heat exchanger 89 by line 88 and then the heated material is fed to the base of column 80 by line 90.

A liquid bottom product is removed from column 60 by line 66 and is fed via line 70 to tray 20 of the 30-tray column 100 at a rate of 285 parts per hour. The approximate conditions within column 100 are: head pressure=50 torr, base pressure=100 torr, base temperature=296° C., head temperature=268° C. Three thousand six hundred seventy (3670) parts per hour of the line 66 stream is circulated through heat exchanger 68 to the base of column 60 by means of lines 67 and 69. A vapor is removed from the top of column 100 at a rate of 711 parts per hour and fed through line 101 to heat exchanger 102 in which the product is condensed. Approximately 75% of the condensed product is recycled via lines 103 and 104 to the top of column 100 and the remainder is removed from the process by line 105. The product obtained via line 105 is substantially pure 2,6-NDC containing 82 ppm 2,6-MFN and 29 ppm 2,6-MHN and is suitable for the manufacture of fiber-grade and film-grade poly(ethylene 2,6-naphthalenedicarboxylate). A liquid column base underflow is removed from column 100 through line 106 and recycled to esterification reactor 10 (FIG. 1) by means of line 5 at the rate of 47.9 parts per hour. Seven hundred ninety three (793) parts per hour from stream 106 are circulated through heat exchanger 108 and to the base of column 100 by lines 107 and 109 to provide the heat required for the operation of column 100. The energy use of the process is 2,060 Kcal/Kg 2,6-NDC product, and the overall yield from 2,6-NDA to 2,6-NDC is 97.0%.

The composition (weight percentages) of certain of the streams of the process depicted in FIG. 3 and described above are set forth in Table III and o-XYL is o-xylene. The values marked * are parts per million.

TABLE III

| | Stream | | | | |
|---|---|---|---|---|---|
| Component | 61 | 66 | 71 | 87 | 106 |
| 2,6-NDC | 485* | 94.6 | 79.4 | 99.0 | 99.99 |
| 2,6-NDA | — | 0.29 | — | — | — |
| 2,6-MHN | — | 5.14 | 92.0 | 121* | 29.4 |
| TMTM | 1.35 | — | 1.61 | — | — |
| o-XYL | 97.8 | — | 451* | — | — |
| MN | 0.84 | — | — | — | — |
| 2,6-MFN | 86.6 | 72.1* | 0.22 | 0.98 | 85.5 |

The invention has been described in detail with particular reference to preferred embodiments thereof, but it will be understood that variations and modifications can be effected within the spirit and scope of the invention.

I claim:

1. Process for the manufacture of a dialkyl ester of a naphthalenedicarboxylic acid (NDC) which comprises the steps of:
    (1) feeding a lower alkanol and a naphthalenedicarboxylic acid (NDA) to an esterification zone which is maintained at a temperature of about 200 to 350° C. to obtain a crude esterification product comprising lower alkanol, water, NDC, monoalkyl ester of naphthalenedicarboxylic acid (MHN), NDA, trialkyl trimellitate (TATM) and catalyst residues;
    (2) removing liquid and vapor streams comprising crude esterification product from the esterification zone;
    (3) reducing the pressure of the liquid and vapor streams of step (2) and feeding the streams to the lower section of a primary flash distillation column to produce (i) an overhead vapor stream rich in the NDC, alkanol and water and (ii) column base underflow stream rich in NDA, MHN and NDC;
    (4) recycling a major portion of the underflow stream of step (3) to the esterification zone;
    (5) feeding a minor portion of the underflow stream of step (3) to a secondary flash vessel to produce a (i) vapor stream comprising NDC, MHN and NDA and (ii) liquid residue stream comprising TATM, catalyst residues, NDC, MHN and NDA;
    (6) feeding the overhead vapor stream from step (3) and the vapor stream from step (5) to the mid-section of a distillation column to obtain (i) an overhead vapor stream rich in alkanol and water and (ii) a column base underflow stream rich in NDC and essentially devoid of alkanol and water;
wherein all of the heat for the primary flash distillation column and the secondary flash vessel is provided by the heat of the streams fed to the column and vessel.

2. Process acording to claim 1 wherein step (1) is carried out at a temperature of about 250 to 320° C. and a pressure of about atmospheric to 55 bar gauge.

3. Process according to claim 2 wherein the NDA contains about 0.1 to 1 weight percent trimellitc acid ad up to 10,000 parts per million by weight cobalt and/or manganese catalyst residues.

4. Process according to claim 1 which includes the steps of:
    (7) feeding the column base underflow stream from step (6) to the mid-section of a third distillation column to remove MFN and obtain a column base underflow stream rich in NDC, MHN and NDA; and
    (8) feeding the column base underflow stream from step (7) to the mid-section of a fourth distillation column to obtain (i) an overhead vapor stream comprising substantially pure NDC and (ii) a column base undeflow stream rich in MHN and NDA.

5. Process for the manufacture of a dimethyl of 2,6-naphthalenedicarboxylic acid (2,6-NDC) which comprises the steps of:
    (1) feeding methanol and 2,6-naphthalenedicarboxylic acid (2,6-NDA) to an esterification zone which is maintained at a temperature of about 250 to 320° C. and a pressure of about atmospheric to 55 bar gauge to obtain a crude esterification product comprising lower alkanol, water, 2,6-NDC, monomethyl ester of 2,6-naphthalenedicarboxylic acid (2,6-MHN), 2,6-NDA, trimethyl trimellitate (TMTM) and catalyst residues;
    (2) removing liquid and vapor streams comprising crude esterification product from the esterification zone;
    (3) reducing the pressure of the liquid and vapor streams of step (2) and feeding the streams to the lower section of a primary flash distillation column to produce (i) an overhead vapor stream rich in the 2,6-NDC, methanol and water and (ii) column base underflow stream rich in 2,6-NDA, 2,6-MHN and 2,5-NDC;
    (4) recycling a major portion of the underflow stream of step (3) to the esterification zone;
    (5) feeding a minor portion of the underflow stream of step (3) to a secondary flash vessel to produce a (i) vapor stream comprising 2,6-NDC, 2,6-MHN and 2,6-NDA and (ii) liquid residue stream comprising TMTM, catalyst residues, 2,6-NDC, 2,6-MHN and 2,6-NDA;
    (6) feeding the overhead vapor stream from step (3) and the vapor stream from step (5) to the mid-section of a distillation column to obtain (i) an overhead vapor stream rich in methanol and water and (ii) a column base underflow stream rich in 2,6-NDC and essentially devoid of methanol and water;
wherein all of the heat for the primary flash distillation column and the secondary flash vessel is provided by the heat of the streams fed to the column and vessel.

6. Process according to claim 5 which includes the steps of:

(7) feeding the column base underflow stream from step (6) to the mid-section of a third distillation column to remove 2,6-MFN and obtain a column base underflow stream rich in 2,6-NDC, 2,6-MHN and 2,6-NDA; and (8) feeding the column base underflow stream from step (7) to the mid-section of a fourth distillation column to obtain (i) an overhead vapor stream comprising substantially pure 2,6-NDC and (ii) a column base underflow stream rich in 2,6-MHN and 2,6-NDA.

* * * * *